United States Patent [19]

Vrieland

[11] 3,935,126

[45] Jan. 27, 1976

[54] CATALYST AND METHOD OF OXYDEHYDROGENATION OF ALKYL AROMATIC COMPOUNDS

[75] Inventor: G. Edwin Vrieland, Midland, Mich.

[73] Assignee: The Dow Chemical Company, Midland, Mich.

[22] Filed: May 28, 1974

[21] Appl. No.: 474,128

[52] U.S. Cl. .............. 252/437; 252/435; 260/290; 260/329; 260/624; 260/650; 260/651; 260/669
[51] Int. Cl.² .......................................... B01J 27/18
[58] Field of Search ........................... 252/437, 435

[56] References Cited
UNITED STATES PATENTS

| | | |
|---|---|---|
| 2,693,496 | 11/1954 | Box .............................. 252/437 X |
| 2,843,640 | 7/1958 | Langlois et al. ................ 252/437 X |
| 2,934,551 | 4/1960 | Stringer .......................... 252/437 X |
| 3,462,495 | 8/1969 | Friedli ............................ 252/437 X |
| 3,541,172 | 11/1970 | Stowe et al. ................... 252/437 X |

*Primary Examiner*—Patrick P. Garvin
*Attorney, Agent, or Firm*—Stephen Hoynak; Glwynn R. Baker

[57] ABSTRACT

Alkaline earth-nickel phosphates having from about 61% to about 70% phosphate are superior catalysts for oxydehydrogenating alkyl aromatic compounds including nitrogen heterocyclics which have at least one $C_2$–$C_6$ alkyl side chain to form derivatives having side chain unsaturation. The alkyl aromatic compound can have 1–2 rings. The process is carried out at 450°–650°C. and a space velocity of 55–2500.

6 Claims, No Drawings

CATALYST AND METHOD OF OXYDEHYDROGENATION OF ALKYL AROMATIC COMPOUNDS

BACKGROUND OF THE INVENTION

Certain alkaline earth-nickel phosphates, such as calcium-nickel phosphate or strontium-nickel phosphate are good dehydrogenation catalysts for converting n-butenes to butadiene or for oxydehydrogenating lower aliphatic alkanes and alkenes to dienes. Although they also dehydrogenate alkyl aromatic hydrocarbons to their alkene aromatic derivatives, these catalysts are not as active for this purpose, as are the well known self-regenerative catalysts containing iron, zinc or magnesium oxides and potassium oxide or a potassium compound convertible to the oxide.

One of the shortcomings of the self-regenerative dehydrogenation catalysts for converting ethyl benzene to styrene is that under acceptable commercially operating conditions the conversion of the ethyl benzene is in the 35–40% range. Selectivity, however, is in the 85–95% range. The self-regenerative catalysts are not sufficiently selective in oxydehydrogenation systems to be useful commercially for converting alkyl benzenes to alkene derivatives in the presence of oxygen.

Therefore, an object of this invention is the provision of a superior catalyst for oxydehydrogenation of an alkyl aromatic compound. Another object is to provide a process for oxydehydrogenating alkyl aromatic compounds in which process superior conversions with high selectivities of the alkyl group to an alkene group are obtained.

SUMMARY OF THE INVENTION

This invention concerns a novel catalyst and a method of oxydehydrogenating alkyl aromatic compounds having at least one $C_2$–$C_6$ alkyl group; including nitrogen heterocyclics, and 1–2 rings in the aromatic moiety, to form derivatives having aliphatic unsaturation in the side chain. More particularly, the catalyst is an alkaline earth nickel-phosphate which has been impregnated with phosphate ions. The catalyst can also contain small amounts of chromium oxide. The method comprises passing a mixture of an oxygen containing gas and vapors of the alkyl aromatic compounds, with or without an inert diluent vapor, over the catalyst at a temperature of from about 450°C. to about 650°C., at a space velocity of from about 55 to about 2500.

DETAILED DESCRIPTION OF THE INVENTION

A commercially available calcium nickel phosphate catalyst is made by the procedure described in U.S. Pat. No. 2,542,813. In general, the procedure comprises preparing an aqueous solution of calcium chloride, and nickel nitrate in a molar ratio of about 8 to 1, respectively, and about 9% excess $H_3PO_4$. This solution is fed into a tank simultaneously with ammonia to control the pH at between 7.7 to 8.3. The precipitate which forms is separated washed and dried. The dried product is then crushed, mixed with a lubricant and if desired with about 1 to 5% chromium oxide. The mixture is then formed into pellets or classified by screening.

Strontium nickel phosphate and other alkaline earth metal-nickel phosphates can be prepared by following the above-described procedure or they can be prepared by procedures described in U.S. Pat. No. 3,541,172. In preparing the catalysts of this invention it is necessary to remove any lubricant from the alkaline earth-nickel phosphate before impregnating with phosphate ions.

The amount of phosphate on and in the alkaline earth metal phosphate can range from about 61% to about 70%. If the alkaline earth-nickel phosphate is immersed in a solution with a concentration of more than about 0.15 mole per liter of phosphate or less than about 3.5 moles per liter, good results are obtained. When the concentration is below 0.15 molar phosphate, conversion and selectivity of the oxydehydrogenation reaction are comparatively low, and when the concentration is above 3.5 molar phosphate, conversion tends to decrease, but selectivity remains fairly high.

The molar ratio of oxygen to alkyl aromatic compound can range from about 0.5 to about 4.0 moles of $O_2$ per mole of alkyl aromatic compound, but a preferred range is from about 0.5 to about 1.5 and most preferred is a range of about 0.9 to about 1.1 moles $O_2$ per mole of aromatic compound.

The oxygen can be pure oxygen, air, or air enriched with oxygen.

The space velocity (vol./vol./hr.) can range from about 55 to 2500, but a preferred range is from about 250 to about 1800. Most preferred is a range of from about 800 to about 1800.

Diluents when used can be the noble gases, nitrogen, carbon dioxide or steam. These can range from about 4–16 volumes per volume of alkyl aromatic compound, but preferably range from about 4 to about 11 volumes.

The pressure at which the reaction can be run ranges from 0.5 to about 5 atmospheres, but it is preferable to operate at autogenous pressure which is generally the range of about 1 to about 2 atmospheres.

The reaction can be effected in a temperature range of from about 450°C. to about 650°C., but a preferred range is from about 500°C. to about 575°C.

Care should be exercized to avois explosive mixtures when feeding the alkyl aromatic compound and oxygen into the reactor.

The examples which follow are intended to illustrate, but not to limit the invention. All parts are by weight unless specifically indicated otherwise.

EXAMPLE 1

Pellets of a commercial grade of calcium-nickel phosphate containing graphite, but no chromates, were crushed and calcined in air at 650°C. for 9 hours to remove the graphite. An aqueous solution of 2.2 molar $NH_4H_2PO_4$ neutralized with ammonium hydroxide was added to 2 l. of 5–12 mesh particles of the calcium-nickel phosphate. After 15 minutes soaking the solids were separated, partially dried at room temperature and further dried at 110°C. for 16 hours. The phosphate impregnated solids were then calcined in flowing air at gradually increasing temperatures up to 550°C.

Unless otherwise indicated the reactor for this and subsequent examples was a high silica glass tube 16 mm I.D. and 42 cm. long, with an inlet for the compound to be dehydrogenated and another for a premixed feed of oxygen and an inert diluent. After loading the reactor with catalyst, coarse, high silica chips were placed above the catalyst layer to serve as a mixing and preheating area. The reactor was heated by placing it in an electric resistance furnace.

The reactor was loaded with 20 ml. of the phosphate impregnated calcium-nickel phosphate, and then high silica chips were loaded on top of the catalyst.

A feed of 51.6 ml. air, 22.5 ml. nitrogen per minute and 2.58 g. of ethyl benzene was passed through the catalyst bed which was held at 535°C. After three hours the conversion of ethyl benzene fed was 77.2% and the selectivity to styrene was 89.5%. After 22 hours of continuous operation conversion was 69.2% and selectivity was 87.1%.

EXAMPLE 2

The catalyst for this run was prepared by soaking calcined calcium-nickel phosphate particles of 5–12 mesh size in a 1.5 molar aqueous phosphoric acid solution. The catalyst was then dried by the process described in Example 1.

For this run 60 ml. per minute of helium, 15 ml. per minute of $O_2$ and 3.2 g. per hour of ethyl benzene were passed over 20 ml. of the catalyst. After three hours at 536°C. the conversion was 70% and selectivity to styrenes was 88.9%.

EXAMPLE 3

Strontium nickel phosphate particles, of 5–12 mesh size, were soaked in a 14.7 weight percent solution of $NH_4H_2PO_4$, followed by drying and calcining as described in Example 1.

Feed at a rate of 60 ml. per minute of helium, 15 ml. per minute of oxygen and 3.2 g. per hour of ethyl benzene was passed over 20 ml. of the catalyst at 531°C. After 23 hours the conversion of ethyl benzene was 64.6% and selectivity to styrene was 88.3%.

EXAMPLE 4

One run was made with calcium-nickel phosphate containing about 2% chromium oxide and another with strontium-nickel phosphate containing about 2% chromium oxide. In each instance 5–12 mesh particles were soaked in a 14.7 weight percent aqueous solution of $NH_4H_2PO_4$, and dried and calcined at a temperature of 550°C. The feed rate in each run was 63.2 ml. nitrogen per minute, 10.9 ml. oxygen per minute and 2.62 g. of ethyl benzene per hour. The feed in each instance was passed over 20 ml. of catalyst at 535°C. After 22 hours, the conversion with phosphated strontium-nickel phosphate was 69% and selectivity to styrene was 88%; with the phosphated calcium-nickel phosphate after 11 hours the conversion was 67.8% and selectivity 87%.

EXAMPLE 5

A series of catalysts was prepared using the procedure of Example 1 by soaking calcium-nickel phosphate in various molar concentrations of $NH_4H_2PO_4$ neutralized with ammonia. In each instance 20 ml. of catalyst was tested at 535°C. The feed rates of air nitrogen and ethyl benzene were the same as those of Example 1. Results after 4 hours are tabulated below.

| Molarity of $PO_4$ In Solution | % Conversion E.B. | $O_2$ | % Selectivity To Styrene |
|---|---|---|---|
| 3.48 | 63.3 | 91.9 | 89.4 |
| 2.17 | 66.7 | 94.0 | 89.1 |
| .87 | 65.9 | 96.1 | 90.0 |
| .44 | 66.8 | 96.9 | 89.4 |
| .17 | 49.0 | 100 | 84.0 |
| 0 | 33.7 | 100 | 75.6 |

E.B. = Ethyl Benzene

These data show that a minimum concentration of about 0.15 molar phosphate concentration in solution is needed to show a substantial improvement in conversion and selectivity as compared to the nonphosphated calcium-nickel phosphate. At about 3.5 mol phosphate concentration, conversion of ethyl benzene has passed its peak slightly, but good selectivity is retained.

EXAMPLE 6

A phosphated calcium-nickel phosphate prepared by the procedure of Example 1, was used to convert ring chlorinated ethyl benzene to chlorostyrene. In this run air at 51.6 ml. per minute, nitrogen at 22.5 ml. per minute and chloroethyl benzene (a mixture of 67% ortho and 33% para isomers) at 3.2 g. per hour were fed over 20 ml. of the catalyst at 540°C. The conversion was 64.5% and selectivity to chlorostyrene was 81%.

EXAMPLE 7

A phosphated calcium-nickel phosphate prepared by the procedure of Example 1, with the exception that graphite was removed by calcining at 650°C. in a stream of two parts air and 5.4 parts steam at a GHSV of 440 per hour. The calcium-nickel phosphate was phosphatized with $NH_4H_2PO_4$ and thereafter heated to 550°C. The reactor was loaded with 10 ml. (8.79 g.) of the catalyst. The feed rate to the reactor was 55 ml. air per minute and 4.8 g. of bromoethylbenzene (a mixture containing about 25% o-bromoethylbenzene and 75% p-bromoethylbenzene). The operation was cyclic in that an oxydehydrogenation period of two hours at 500°C. was followed by a half hour decoking cycle. The conversion was 83.3% and selectivity to bromostyrene was 86.7%.

In a continuous run at 475°C. using 20 cc of catalyst and feeding 51.6 ml. of air per minute, 22.5 ml. nitrogen per minute and 4.78 g. of the bromoethylbenzene per hour, the conversion was 73.9% and selectivity to bromostyrene was 85% average from 6–12 hours on stream.

EXAMPLE 8

The reactor in this run was a ¾ inch I.D. stainless steel tube loaded with 704 g. of a catalyst prepared as in Example 1.

The feed rate was 1.26 standard cubic feet per hour of ethylbenzene, 6.48 SCHF air and 2.55 SCHF nitrogen to provide a GHSV of 420 hr. $^{-1}$. The reaction temperature was 555°C. The reaction was run for 40.5 days without catalyst burnoff. After a total of 50 days on stream the conversion was 65% and selectivity to styrene was 84%.

EXAMPLE 9

The reactor described in Example 1 was loaded with 20 ml. (17.27 g.) of a catalyst prepared by the procedure of Example 1.

The feed rate in each case was about 24.8 mmoles per hour of hydrocarbon, and 28.4 mmoles of oxygen, with air as the oxygen source. The GHSV was 195 hr. $^{-1}$.

A variety of alkyl aromatic compounds were passed over the catalyst at various temperatures. Tabulated below are the results of these runs.

| Alkyl Aromatic In Feed | Temp. °C. | % Conversion | % Selectivity |
|---|---|---|---|
| m-diethylbenzene | 500 | 53.4 | 59.9 m-vinyl ethylbenzene 14.5 divinyl benzene |
| p,t-butylethylbenzene | 500 | 52.1 | 77.8 p,t-butyl styrene |
| o,p-ethyl toluene | 500 | 36.4 | 67.7 o,p-vinyl toluene |
| 1 & 2 ethyl naphthalene | 500 | 51.4 | 82.7 1 and 2 vinyl naphthalene |
| 2-ethyl pyridine | 500 | 37.9 | 48.9 2-vinyl pyridine |
| 2-ethyl thiophene | 464 | 78.8 | 79.5 2-vinyl thiophene |
| 3-ethyl phenol | 458 | 57.7 | 64.4 3-vinyl phenol |

I claim:

1. A catalyst consisting essentially of an alkaline earth metal-nickel phosphate containing from about 61 to about 70% phosphate.

2. A catalyst of claim 1 in which the alkaline earth metal moiety is calcium.

3. A catalyst of claim 1 in which the alkaline earth metal moiety is strontium.

4. A method of preparing a catalyst having from about 61 to about 70% phosphate consisting essentially of impregnating an alkaline earth-nickel phosphate with an aqueous solution having a concentration from about 0.15 to about 3.5 moles of phosphate per liter and thereafter drying the catalyst.

5. The method of claim 4 is which the alkaline earth nickel phosphate is calcium-nickel phosphate.

6. The method of claim 4 in which the alkaline earth metal phosphate is strontium nickel phosphate.

* * * * *

UNITED STATES PATENT AND TRADEMARK OFFICE
CERTIFICATE OF CORRECTION

PATENT NO. : 3,935,126
DATED : January 27, 1976
INVENTOR(S) : G. Edwin Vrieland

It is certified that error appears in the above-identified patent and that said Letters Patent are hereby corrected as shown below:

Column 1, line 44, "chronium" should read --chromium--;

Column 2, line 38, "avois" should read --avoid--;

Column 4, line 36, "83.3%" should read --86.3%--;

Column 6, line 18, "catalyt" should read --catalyst--;

Column 6, line 19, "is" should read --in--.

Signed and Sealed this twenty-fifth Day of May 1976

[SEAL]

Attest:

RUTH C. MASON
Attesting Officer

C. MARSHALL DANN
Commissioner of Patents and Trademarks